United States Patent [19]
Lang

[11] Patent Number: 5,383,447
[45] Date of Patent: Jan. 24, 1995

[54] DEVICE FOR WARMING AND MOISTENING GASES HAVING BOTH AN ACTIVE AND PASSIVE HEAT EXCHANGER.

[76] Inventor: Volker Lang, Zugspitzstrasse 52, Gauting, Germany, 8035

[21] Appl. No.: 50,145

[22] PCT Filed: Oct. 31, 1991

[86] PCT No.: PCT/EP91/02060
§ 371 Date: Jun. 6, 1993
§ 102(e) Date: Jun. 6, 1993

[87] PCT Pub. No.: WO92/07601
PCT Pub. Date: May 14, 1992

[30] Foreign Application Priority Data

Nov. 2, 1990 [DE] Germany .................. 4034969
Aug. 6, 1991 [DE] Germany .................. 4126028

[51] Int. Cl.⁶ ............... A62B 18/08; A61M 16/00; F23D 11/00; F24J 3/00
[52] U.S. Cl. .................. 128/201.13; 128/203.26; 128/204.17; 392/396
[58] Field of Search .............. 128/201.13, 203.26, 128/204.17; 392/394–396, 403, 406; 261/94, 99; 165/119, 60, 66–68, 72–75, 104.13

[56] References Cited

U.S. PATENT DOCUMENTS

| | | | |
|---|---|---|---|
| 3,638,926 | 2/1972 | Melville et al. | 128/201.13 |
| 3,659,604 | 5/1972 | Melville et al. | 128/201.13 |
| 3,912,795 | 10/1975 | Jackson | 261/36 R |
| 3,916,891 | 11/1975 | Freytag et al. | 128/201.13 |
| 3,982,095 | 9/1976 | Robinson | 128/201.13 |
| 4,048,993 | 9/1977 | Dobritz | 128/201.13 |
| 4,060,576 | 11/1977 | Grant | 128/201.13 |
| 4,529,867 | 7/1985 | Velnosky et al. | 128/201.13 |
| 4,618,462 | 10/1986 | Fisher | 128/201.13 |
| 5,062,145 | 10/1991 | Zwaan et al. | 392/396 |
| 5,109,471 | 4/1992 | Lang | 128/201.13 |

FOREIGN PATENT DOCUMENTS

| | | |
|---|---|---|
| 0413127 | 2/1991 | European Pat. Off. . |
| 0258928 | 3/1998 | European Pat. Off. . |
| 2250542 | 6/1975 | France . |
| 2636845 | 3/1990 | France . |

Primary Examiner—Kimberly L. Asher
Attorney, Agent, or Firm—Jacobson, Price, Holman & Stern

[57] ABSTRACT

A device for heating and moistening respiratory gases with a small volume of dead space which is especially suitable for giving artificial respiration to premature and newborn infants and children. This device includes three parts, whereby two parts, largely made of metal, are interconnected in a housing and form a connecting component combined with an active steam-sterilizable moistening and heating device into which a third part, a one-time heating-moistening exchanger insert, is fitted. The upper third of this insert acts as a passive heat-moisture exchanger which premoistens and preheats the dry respiratory gas on inspiration (about 30° C., 100% relative humidity) and the central and lower third of which, supported by the active moistening device and heating with the aid of the active heat-moisture device, finally undertakes the optimum conditioning of the respiratory gas (36–37° C., 100% r.h.). On expiration, 60–80% of the moisture and heat of the optimally warm and damp respiratory gas is recovered by the heat-moisture exchanger insert primarily via its upper third away from the patient. In cases of great respiratory difficulty, e.g. in very small premature infants, the volume of dead space of the device can be reduced still further by opening an air outlet stub in the third part.

7 Claims, 2 Drawing Sheets

DEVICE FOR WARMING AND MOISTENING GASES HAVING BOTH AN ACTIVE AND PASSIVE HEAT EXCHANGER.

FIELD OF THE INVENTION

The invention relates to an apparatus for warming and moistening gases, more particularly, breathing gases during artificial respiration, comprising the combination of at least one passive heat and moisture exchanger and at least one active warming and moistening device.

BACKGROUND OF THE INVENTION

Under physiological conditions, the nose functions to provide active warming and heating of breathing air. When a patient is undergoing artificial respiration however the nose is shunted by a flexible tube, whose end is inserted into the trachea. The moistening and warming action on the breathing gases, which is absolutely essential for normal function of the lungs, is presently performed by an apparatus, which more particularly operates in accordance with two principles. A first part of the apparatus actively imparts heat and moisture to the air. In this case for instance dry, cold air is caused to pass through an electrically heated water bath moistener and thereby conditioned prior to being supplied to the patient. A second part of the apparatus operates passively as a heat and moisture exchanger (H. M. E.). In this case heat and moisture are removed from the moist, warm expired air and are then imparted to the cold, dry air to be inspired without an additional active supply of heat and moisture from the surroundings taking place.

In accordance with this prior art it is admittedly possible for the apparatus to supply sufficiently tempered and moistened respiratory air when there is an active supply of heat and moisture, but however very involved technical and nursing measures are necessary so that production and running costs of such equipment are very high. In contradistinction to such apparatus, there are less complex, simply designed and simply operated passive heat and moisture exchangers, but they have not so far provided a sufficient moistening and warming action for artificial respiration.

In an earlier application, see European patent publication 0 413 127 A2, the applicant has described an apparatus for warming and moistening breathing air for artificial respiration of the type initially mentioned in the case of which the above mentioned advantages are obtained by a combination of independent passive heat and moisture exchangers with an active heat and moisture exchanger. However, this prior art device is relatively complex in design. Furthermore, such a device involved some problems owing to there being an excessive dead volume, which due to the re-inspiration of exhaled air had a particularly pronounced effect in the case of newly born babies, owing to their small vital capacity.

SUMMARY OF THE INVENTION

One object of the present invention is accordingly to provide an apparatus of the type initially mentioned which optimally supplies moistened breathing air with small dead volumes and in this respect is very simple in design and is simple to operate.

In accordance with the invention, a heat and moisture exchanger insert is provided mounted in a housing and one part operates as a passive heat and moisture exchanger and another part operates as an active heat and moisture exchanger with the heating and moistening device surrounding it. This means that there is a single unit comprising both a passive heat and moisture exchanger and an active heating and humidifying device. The advantages of both principles are consequently realized in a constructionally compact design as a simple apparatus so that on one hand there is optimum moistening and heating of the breathing gases while at the same time there is a low degree of technical complexity, little nursing attention is required, while costs are low.

In accordance with a further advantageous development of the invention, the apparatus is so designed that its housing is divided into two parts, an upper housing part being in the form of a conical connecting part with a cylindrical cavity to receive the passive heat and moisture exchanger insert or cartridge and a lower housing part being in the form of an active moistening and heating device, into which an adapter can be received for the tube which is to be inserted into the patient.

BRIEF DESCRIPTION OF THE DRAWINGS

Further advantages of the invention will be understood from the following detailed descriptive disclosure of one embodiment illustrated in the accompanying drawings.

DETAILED DESCRIPTION OF THE PREFERRED EMBODIMENTS

Figure 1:
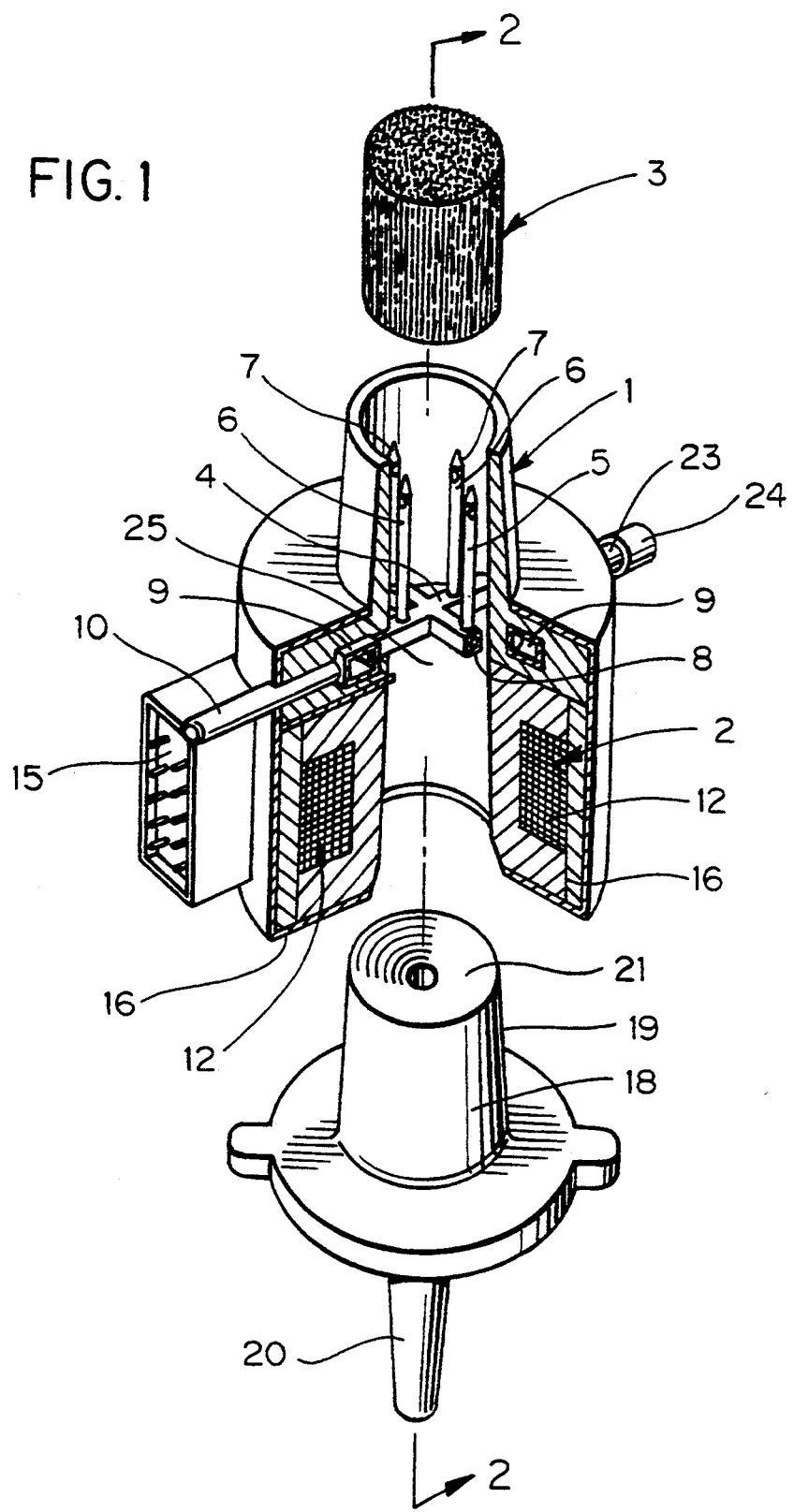
FIG. 1 is a perspective, exploded view of the working embodiment which is made in three parts.
Figure 2:
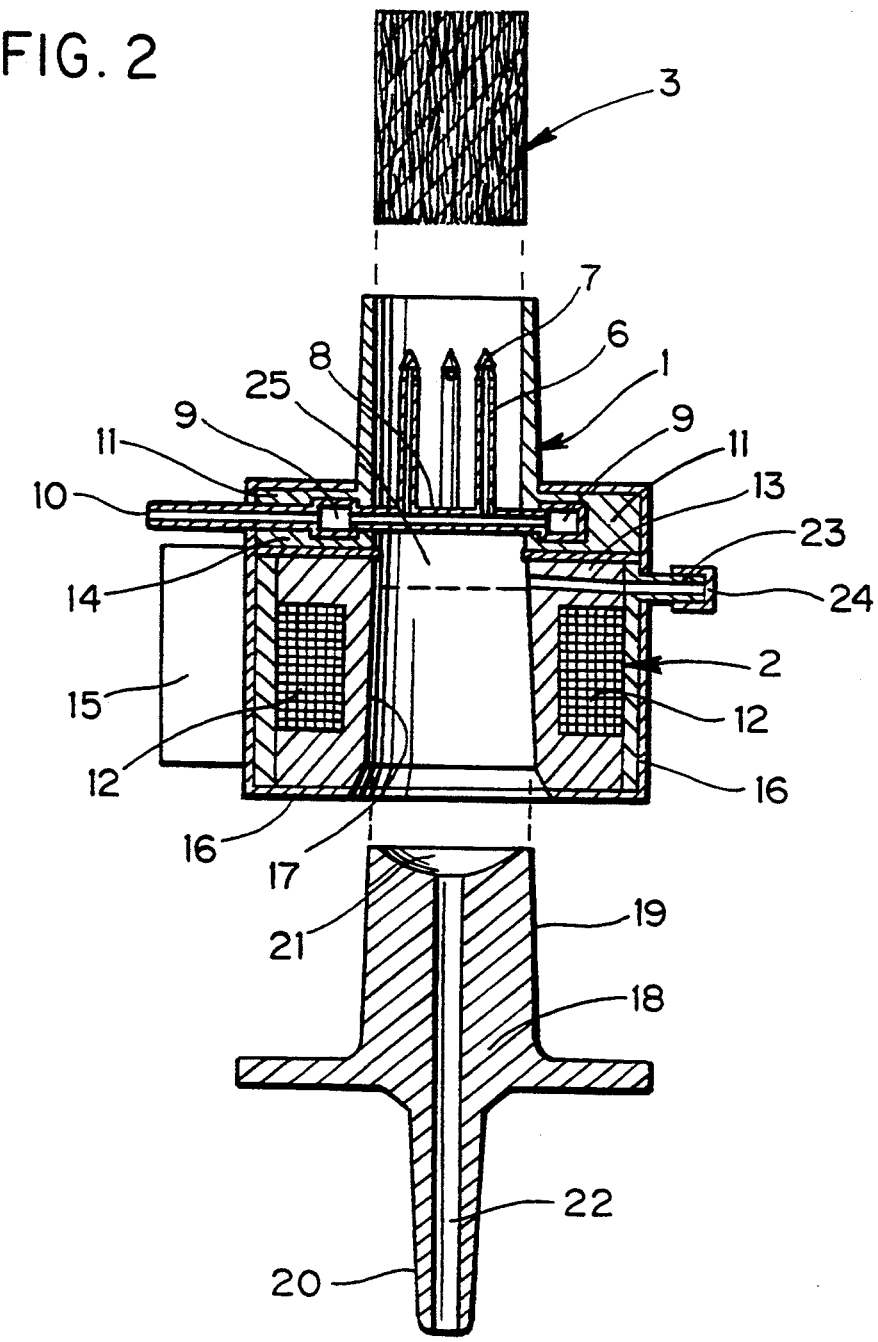
FIG. 2 shows a section in an exploded view taken along the line II—II of FIG. 1.

The apparatus in accordance with the invention comprises three parts, including a connecting member part 1 and a heating connecting part 2 fabricated mostly of metal and being permanently connected with one another.

The part 1 constitutes a connecting member for a Y adapter or the respiration head of an artificial respiration flexible tube system, via which the breathing gases are supplied during the inhalation phase and are abducted in the exhalation phase. This connecting member 1 is designed in the form of a metallic cylindrical tube or hollow cylinder, which on the outside is provided with a standardized connection cone. Before use, a snugly fitting cylindrical heat and moisture exchanger insert 3 is introduced into its lumen, which contains an exchange medium, such as, for example, a commercially available H. M. E. as produced by the Company ICOR AB of Sweden, so that a lowermost edge 5 of the insert 3 abuts the cruciform internal fitting 4. Four metal tubelets 6 extend from and perpendicular to fitting 4. The tubelets 6 terminate in tips with lateral openings 7. The ends of the tubelets extend into the center third of the heat and moisture exchanger insert 3 and supply the insert 3 with exactly metered tempered sterilized water, which is supplied to the tubelets via an external, known metering device by way of flexible tube ports 10, an annular channel 9 and the fine tubes 8 of the cruciform internal fitting 4. The annular channel 9 is connected via its metallic casing 11 in a thermally conductive manner with the heating connecting part 2 of the apparatus. The heating element 12 installed in part 2 and the two temperature sensors 13 and 14 are supplied via an external connecting cable and a multi-pin plug 15 with electrical power for exact monitoring and control. The synthetic resin casing 16 serves for heat insulation of the heating part 2, whereas the standardized inner cone 17 serves for a reliable and simultaneously releasable connection of the inserted tube adapter 18 with the standardized external cone 19. The port 23 is shut off by a removable cap 24. A shallow cavity 25 is formed between the tube adapter 19 and a lower side of the cruciform internal fitting 4 when the tube adapter 19 is inserted into cone 17. The port 23 connects cavity 25 and the area surrounding the apparatus.

A description will be provided of the operation of the invention explained with reference to a working embodiment. Dry, cold breathing gas (at approximately 20° C. with a relative humidity of approximately 10%) passes during the inhalation phase from an artificial respirator, not illustrated in the drawing, via the patient flexible tube system with a Y adapter secured to the connecting member 1. Thence the breathing gas flows through the heat and moisture exchanger insert 3 (H. M. E. insert or cartridge). In its upper third, the insert 3 overwhelmingly functions as a passive H. M. E., in which cold breathing gas is passively warmed in a first stage and is pre-humidified by stored heat and moisture, which have previously been abstracted from the exhaled air of the patient on which artificial respiration is being performed. The breathing gas will however here only attain a temperature of approximately 30° C. at 100% relative humidity. For this reason in a second stage in the center and lower thirds of the H. M. E. insert, active post-moistening and post-heating of the breathing air are performed with the result that via the center lumen 21 and 22 of the flexible tube adapter 18 and through a tracheal tube slipped onto the cone 20, the air will then reach the trachea of the patient at a temperature of 36 to 37° C. at 100% relative humidity. This active post-moistening and post-heating is performed in such a manner that by using an external controller, exactly metered water and electrical heating power is supplied to the above mentioned device. This will lead to heating of the metal parts of the apparatus, more particularly however, owing to the additional emergence of heated water via the tubelets 6 into the central third of the H. M. E. insert 3 and thence rapidly spreading out owing to the action of gravity into the lower third of the insert 3 so that active heating and moistening take place. Owing to the large surface area of the H. M. E. insert, rapid and optimum conditioning of the passing through air to be inhaled is ensured.

In the exhalation phase the moist gas to be inhaled flows at body temperature (i.e. at 36 to 37° C. at 100% relative humidity) via the flexible tube, first into the tube adapter 18 and then into the actively humidified and warmed lower two thirds of the H. M. E. insert 3 to give up only a little of its total heat and moisture and then in the upper passive third thereof 60 to 80% of its total heat and moisture. This means that in the flexible tube system only a very small quantity of moisture changes into condensate. In comparison with conventional systems there is the additional advantage of economy in nursing attention but furthermore advantages relevant to bacteriological and hygienic aspects.

Since in the apparatus in accordance with the invention the part which is technically most complex, that is to say the connected parts 1 and 2, may be produced in the form of a readily cleaned, steam sterilizable, combined active warming and moistening device with a connecting member, during use there is not only an optimum conditioning of the breathing gases for the patient, but furthermore protection against infection and saving in costs. Owing to the incorporation of two temperature sensors with a following twin-channel electronic temperature monitoring means and controller, and heating of the moistening device to a temperature only slightly above body temperature and with only a small heat capacity, it is possible for reliable artificial respiration of the patient to take place without excessively heated breathing gases even when operating under extreme conditions. Moreover owing to the small dead volume, objectionable re-inspiration of exhaled air is not to be feared in the case of babies and children. In particularly difficult artificial respiration situations, as for instance in artificial respiration of premature babies with high respiration rates and small vital capacities it is possible to arrange for a further reduction in functional dead volume by opening the venting port 23 by removal of the closure cap 24. The spent, exhaled air thereby passes via the cavity 25 and the port 23 opening thereinto directly into the surroundings.

I claim:

1. An apparatus for warming and moistening gases, more particularly breathing gases during artificial respiration, including the combination of at least one passive heat and moisture exchanger and at least one active warming and moistening device, said apparatus comprising:

a housing, a heat and moisture exchanger insert mounted in said housing and operating as a passive heat and moisture exchanger and as an active heat and moisture exchanger, said housing including a first housing part having an annular channel and a second housing part with a cruciform insert arranged between said first housing part and said second housing part, said cruciform insert including channels connected with said annular channel of said first housing part and said cruciform insert having tubelets in communication with said annular channel, said tubelets having open ends communicating with said heat and moisture exchanger insert.

2. The apparatus as claimed in claim 1, wherein said first housing part is a conical connecting part with a cylindrical cavity for receiving said heat and moisture exchanger insert and said second housing part is an active moistening and heating device.

3. The apparatus as claimed in claim 1, wherein said open ends of said tubelets extend into a center third of said heat and moisture exchanger insert.

4. The apparatus as claimed in claim 1, wherein said cruciform insert includes arms extending between said tubelets and said annular channel.

5. The apparatus as claimed in claim 1, wherein said first and said second housing parts are made of metal and are at least partly covered with a thermally insulating synthetic resin casing.

6. The apparatus as claimed in claim 1, wherein a flexible tube adapter is inserted into said second housing part.

7. The apparatus as claimed in claim 1, wherein said second housing part includes a venting port connected with the surroundings and said venting port is closed by a removable cap.

* * * * *